US011013707B2

(12) United States Patent
Orndorff et al.

(10) Patent No.: US 11,013,707 B2
(45) Date of Patent: *May 25, 2021

(54) ADMINISTRATION OF ORAL METHYLDOPA

(71) Applicants: ImmunoMolecular Therapeutics, LLC., Denver, CO (US); The Regents of the University of Colorado, a body corporate, Denver, CO (US)

(72) Inventors: Steve Orndorff, Broomfield, CO (US); Aaron Michels, Aurora, CO (US)

(73) Assignees: The Regents of the University of Colorado, a body corporate, Denver, CO (US); ImmunoMolecular Therapeutics, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/934,790

(22) Filed: Mar. 23, 2018

(65) Prior Publication Data

US 2019/0290607 A1  Sep. 26, 2019

(51) Int. Cl.
| | |
|---|---|
| *A61K 31/295* | (2006.01) |
| *A61K 9/00* | (2006.01) |
| *A61K 9/20* | (2006.01) |
| *A61K 9/48* | (2006.01) |
| *A61K 31/195* | (2006.01) |

(52) U.S. Cl.
CPC .......... *A61K 31/195* (2013.01); *A61K 9/0053* (2013.01); *A61K 9/20* (2013.01); *A61K 9/4808* (2013.01)

(58) Field of Classification Search
None
See application file for complete search history.

(56) References Cited

U.S. PATENT DOCUMENTS

| | | | |
|---|---|---|---|
| 4,207,890 A | 6/1980 | Mamajek et al. | |
| 4,434,153 A | 2/1984 | Urquhart et al. | |
| 4,691,018 A | 9/1987 | Mori et al. | |
| 4,735,804 A | 4/1988 | Caldwell et al. | |
| 4,758,436 A | 7/1988 | Caldwell et al. | |
| 4,767,627 A | 8/1988 | Caldwell et al. | |
| 4,783,337 A | 11/1988 | Wong et al. | |
| 5,415,994 A | 5/1995 | Imrich et al. | |
| 5,424,193 A | 6/1995 | Pronovost et al. | |
| 5,475,033 A | 12/1995 | Ohmori et al. | |
| 5,594,100 A | 1/1997 | Wegman | |
| 5,780,057 A | 7/1998 | Conte et al. | |
| 5,939,281 A | 8/1999 | Lehmann et al. | |
| 6,001,567 A | 12/1999 | Brow et al. | |
| 6,207,197 B1 | 3/2001 | Ilium et al. | |
| 6,218,132 B1 | 4/2001 | Spack et al. | |
| 7,144,569 B1 | 12/2006 | Anderson et al. | |
| 7,749,503 B2 | 7/2010 | Tobia et al. | |
| 8,053,197 B2 | 11/2011 | Vandenbark et al. | |
| 8,314,210 B2 | 11/2012 | Wucherpfennig et al. | |
| 9,629,848 B2 | 4/2017 | Eisenbarth et al. | |
| 9,820,957 B2 | 11/2017 | Orndorff et al. | |
| 1,036,328 A1 | 7/2019 | Michels et al. | |
| 2002/0150914 A1 | 10/2002 | Andersen et al. | |
| 2003/0190665 A1 | 10/2003 | Vandenbark | |
| 2004/0096734 A1 | 5/2004 | Calundann et al. | |
| 2004/0137514 A1 | 7/2004 | Steenbakkers | |
| 2004/0253276 A1 | 12/2004 | Sato et al. | |
| 2004/0265327 A1 | 12/2004 | Grassetti et al. | |
| 2005/0222270 A1 | 10/2005 | Olney et al. | |
| 2006/0183670 A1 | 8/2006 | Orban | |
| 2007/0021341 A1 | 1/2007 | Sela et al. | |
| 2007/0196369 A1 | 8/2007 | Hoogenboom et al. | |
| 2007/0243245 A1* | 10/2007 | Heinicke | A61K 9/2081 |
| | | | 424/461 |
| 2008/0194462 A1 | 8/2008 | Wucherpfennig et al. | |
| 2008/0214656 A1 | 9/2008 | Lim et al. | |
| 2010/0172875 A1 | 7/2010 | Phan et al. | |
| 2010/0172920 A1 | 7/2010 | Rottiers et al. | |
| 2010/0233253 A1 | 9/2010 | Kavimandan et al. | |
| 2011/0245334 A1 | 10/2011 | Du et al. | |
| 2012/0171212 A1 | 7/2012 | Eisenbarth et al. | |
| 2012/0195929 A1 | 8/2012 | Eisenbarth et al. | |
| 2013/0017262 A1 | 1/2013 | Mullen et al. | |
| 2013/0115188 A1 | 5/2013 | Fritsche et al. | |
| 2014/0050807 A1 | 2/2014 | Leighton | |
| 2015/0010631 A1 | 1/2015 | Getts | |
| 2018/0116988 A1 | 5/2018 | Anchordoquy et al. | |

FOREIGN PATENT DOCUMENTS

| | | |
|---|---|---|
| EP | 0098475 | 1/1984 |
| JP | S49-027860 | 7/1974 |
| JP | H04-069331 | 3/1992 |
| JP | H09-52847 | 2/1997 |
| WO | WO 84/02843 | 8/1984 |
| WO | WO 94/01775 | 1/1994 |

(Continued)

OTHER PUBLICATIONS

Trivedi et al. (Poster presented at AAPS 2016 Annual Meeting)(2016).*
AA Pharma Inc.'s Prescribing Information for Methyldopa (2010).*
Methyldopa Tablets USP article (2013). Retrieved from <https://dailymed.nlm.nih.gov/dailymed/fda/fdaDrugXsl.cfm?setid=916d802c-91b6-4015-9e57-7ebf7e9bb5ee&type=display> on Jan. 7, 2019.*
Sjoerdsma (Br. J. Clin. Pharmac. (1982), 13, 45-49).*
U.S. Appl. No. 14/341,767, filed Jul. 26, 2014, Eisenbarth et al.
U.S. Appl. No. 15/355,738, filed Nov. 18, 2016, Eisenbarth et al.
U.S. Appl. No. 15/495,132, filed Apr. 24, 2017, Eisenbarth et al.
U.S. Appl. No. 15/817,739, filed Nov. 20, 2017, Orndorff et al.
U.S. Appl. No. 15/894,118, filed Feb. 12, 2018, Orndorff et al.
U.S. Appl. No. 16/357,397, filed Mar. 19, 2019, Orndorff et al.
"T cell ELISpot Assays," ProImmune Ltd., Nov. 2013, 3 pages [retrieved online from: proimmune.com/ecommerce/page.php?page=elispot].

(Continued)

*Primary Examiner* — Patricia Duffy
*Assistant Examiner* — Garen Gotfredson
(74) *Attorney, Agent, or Firm* — Sheridan Ross P.C.

(57) ABSTRACT

Methods of administering methyldopa to a subject in a fasting state to increase bioavailability of the methyldopa.

11 Claims, 1 Drawing Sheet

(56) References Cited

FOREIGN PATENT DOCUMENTS

| WO | WO 94/29696 | 12/1994 |
|----|----|----|
| WO | WO 99/67641 | 12/1999 |
| WO | WO 00/38650 | 7/2000 |
| WO | WO 00/39587 | 7/2000 |
| WO | WO 01/64183 | 9/2001 |
| WO | WO 03/070752 | 8/2003 |
| WO | WO 2004/007528 | 1/2004 |
| WO | WO 2004/110373 | 12/2004 |
| WO | WO 2005/085323 | 9/2005 |
| WO | WO 2010/141883 | 12/2010 |
| WO | WO 2012/162697 | 11/2012 |
| WO | WO 2016/191634 | 12/2016 |

OTHER PUBLICATIONS

Aharoni et al., "Immunomodulation of experimental allergic encephalomyelitis by antibodies to the antigen-la complex," Nature, 1991, vol. 351, pp. 147-150.
Aldomet® (Methyldopa), Merck & Co., Inc., Product Label, (NDA 13-400/S-086, 2004, pp. 3-8.
Ames et al., "Stereochemical Course In Vivo of Alpha-Methyldopa Decasrboxylation in Rat Brains," Biochem. Pharmacology, 1977, vol. 26(19), pp. 1757-1762.
Aoki et al., "NOD mice and autoimmunity," Autoimmun. Rev., 2005, vol. 4, pp. 373-379.
Au et al., "The Metabolism of 14C-Labelled 1-Methyldopa in Normal and Hypertensive Human Subjects," Biochem. J., 1972, vol. 129, pp. 1-10.
Auclair et al., "Comparative pharmacokinetics of D- and L-alphamethyldopa in plasma, aqueous humor, and cerebrospinal fluid in rabbits," Fundamental & Clinical Pharmacology, 1988, vol. 2(4), pp. 283-293.
Badiola et al. "Enantioselective Construction of Tetrasubstituted Stereogenic Carbons through Bronsted Base Catalyzed Michael Reactions: α'-Hydroxy Enones as Key Enoate Equivalent," Journal of the American Chemical Society, Dec. 2014, vol. 136, No. 51, pp. 17869-17881 (Abstract Only).
Boulard et al., "An interval tightly linked to but distinct from the h2 complex controls both overt diabetes (iddl6) and chronic experimental autoimmune thyroiditis (ceatl) in nonobese diabetic mice," Diabetes, 2002, vol. 51, pp. 2141-2147.
Bresson et al., "Moving towards efficient therapies in type 1 diabetes: To combine or not to combine?," Autoimmun Rev, 2007, vol. 6(5), pp. 315-322, 11 pages.
Chung et al., "Competitive Inhibition in Vivo and Skewing of the T Cell Repertoire of Antigen-Specific CTL Priming by an Anti-Peptide-MHC Monoclonal Antibody," J. Immunol., 2001, vol. 167, pp. 699-707.
Cochlovius et al.,"In Vitro and In Vivo Induction of a Th Cell Response Toward Peptides of the Melanoma-Associated Glycoprotein 100 Protein Selected by the TEPITOPE Program," J. Immunol., 2000, vol. 165, pp. 4731-4741.
Corper et al., "A structural framework for deciphering the link between I-Ag7 and autoimmune diabetes," Science, 2000, vol. 288, pp. 505-511.
Crawford et al., "Mimotopes for Alloreactive and Conventional T Cells in a Peptide-MHC Display Library," PLoS. Biol., 2004, vol. 2, p. 0523-0533.
Crawford et al., "Specificity and detection of insulin-reactive CDR+ T Cells in Type 1 diabetes in the nonobese diabetic (NOD) mouse," PNAS, 2011, vol. 108(40), pp. 16729-16734.
Czerkinsky et al., "Reverse ELISPOT assay for clonal analysis of cytokine production. I. Enumeration of gamma-interferon-secreting cells," Journal of Immunological Methods, 1988, vol. 110(1), pp. 29-36.
Daniel et al., "Prevention of type 1 diabetes in mice by tolerogenic vaccination with a strong agonist insulin mimetope," The Journal of Experimental Medicine, 2011, vol. 208(7), pp. 1501-1510.

Demuth et al., "Vaccine delivery with microneedle skin patches in nonhuman primates," Nat. Biotechnol. 2013, vol. 31(12), pp. 1082-1085.
Faideau et al., "Expression of preproinsulin-2 gene shapes the immune response to preproinsulin in normal mice," J. Immunol., 2004, vol. 172, pp. 25-33.
Fairbrother et al., "Effects of Three Plant Growth Regulators on the Immune Response of Young and Aged Deer Mice Peromyscus Maniculatus," Arch. Environ. Contam, Toxicol., 1986, vol. 15, pp. 265-275.
Fife et al., "Insulin-induced remission in new-onset NOD mice is maintained by the PD-1-PD-L1 pathway," J. Experimental Med., 2006, vol. 203, pp. 2737-2747.
Fontenot et al., "Foxp3 programs the development and function of CD4+CD25+ regulatory T cells," Nature Immunology, 2003, vol. 4, pp. 330-336.
Fujisawa et al., "MHC-linked susceptibility to type 1 diabetes in the NOD mouse: further localization of Idd16 by subcongenic analysis," Ann. NY Acad. Sci., 2006, vol. 1079, pp. 118-121.
Fukushima et al., "Combined insulin B:9-23 self-peptide and polyinosinic-polycytidylic acid accelerate insulitis but inhibit development of diabetes by increasing the proportion of CD4+Foxp3+ regulatory T cells in the islets in non-obese diabetic mice," Biochemical and Biophysical Research Communications, 2008, vol. 367, pp. 719-724.
Gillespie et al., "Clinical and Chemical Studies with a-Methyl-Dopa in Patents with Hypertension," Circulation, 1962, vol. 25, pp. 281-291.
Grigoriadis et al., "Alpha-Methyldopa-Induced Autoimmune Hemolytic Anemia in the Third Trimester of Pregnancy," Case Reports in Obstetrics and Gynecology, 2013, 2 pages, 2013:150278.
Hattori et al., "The NOD mouse: recessive diabetogenic gene within the major histocompatibility complex," Science, 1986, vol. 231, pp. 733-735.
Homann et al., "An immunologic homunculus for type 1 diabetes," J. Clin. Invest., 2006, vol. 116, pp. 1212-1215.
Hovhannisyan et al., "The role of HLA-DQ8 beta57 polymorphism in the anti-gluten T-cell response in coeliac disease," Nature, 2008, vol. 456, pp. 534-538.
Hurtenback, "Prevention of Autoimmune Diabetes in Non-Obese Diabetic Mice by Treatment with a Class II Major Histocompatibility Complex-blocking Peptide," Journal of Experimental Medicine, 1993, vol. 177(5), pp. 1499-1504.
Itoh et al., "Thymus and Autoimmunity: Production of CD25+ CD4+ Naturally Anergic and Suppressive T Cells as a Key Function of the Thymus in Maintaining Immunologic Self-Tolerance," J. Immnol. 1999, vol. 162, pp. 5317-5326.
Jasinski et al., "Transgenic Insulin (B:9-23) T-Cell Receptor Mice Develop Autoimmune Diabetes Dependent Upon RAG Genotype, H-2g7 Homozygosity, and Insulin 2 Gene Knockout," Diabetes, 2006, vol. 55, pp. 1978-1984.
Kachapati et al.,"The Non-Obese Diabetic (NOD) Mouse as a Model of Human Type 1 Diabetes." Animal Models in Diabetes Research. Methods in Molecular Biology, 2012, vol. 933, pp. 3-16.
Kanagawa et al., "The role of I-Ag7 β chain in peptide binding and antigen recognition by T cells," Int Immunol., 1998, vol. 9, pp. 1523-1526.
Kmieciak et al. "Human T cells express CD25 and Foxp3 upon activation and exhibit effector/memory phenotypes without any regulatory/suppressor function," Journal of Translational Medicine, 2009, vol. 7, No. 89, 7 pages.
Kobayashi et al., "Conserved T cell receptor alpha-chain induces insulin autoantibodies," Proc. Natl. Acad. Sci. USA., 2008, vol. 105, pp. 10090-10094.
Lee et al., "Structure of a human insulin peptide-HLA-DQ8 complex and susceptibility to type 1 diabetes." Nature Immunology, 2001, vol. 2(6), pp. 501-507.
Leusch et al. "A short primer on benzene, toluene, ethylbenzene and xylenes (BTEX) in the environment and in hydraulic fracturing fluids," Griffith University, Nov. 17, 2010, 8 pages.
Levisetti et al., "The Insulin-Specific T Cells of Nonobese Diabetic Mice Recognize a Weak MHC-Binding Segment in More Than One Form," Journal of Immunology, 2007, vol. 178(10), pp. 6051-6057.

(56) References Cited

OTHER PUBLICATIONS

Levisetti et al., "Weak proinsulin peptide-major histocompatibility complexes are targeted in autoimmune diabetes in mice," Diabetes, 2008, vol. 57, pp. 1852-1860.
Li et al., A computer screening approach to immunoglobulin superfamily structures and interactions: Discovery of small non-peptidic CD4 inhibitors as novel immunotherapeutics, Proc. Natl. Acad. Sci. USA, 1997, vol. 94, pp. 73-78.
Maindonald "Experimental Design," Australian National University, Apr. 2013, 22 pages [retrieved online from: web.archive.org/web/20130411093944/https://maths-people.anu.edu.au/~johnm/planning/expdes.pdf].
Mareeva et al., "Antibody Specific for the Peptide-Major Histocompatibility Complex," J. Biol. Chem., 2004, vol. 279(43), pp. 44243-44249.
Masteller et al., "Peptide-MHC Class II Dimers as Therapeutics to Modulate Antige-Specific T Cell Responses in Autoimmune Diabetes," J. Immunol., 2003, vol. 171, pp. 5587-5595.
Merfeld et al., "The effect of pH and concentration on alpha-methyldopa absorption in man," J Pharm Pharmacol., 1986, vol. 38, pp. 815-822.
Metrano et al. "Peptide-Catalyzed Conversion of Racemic Oxazol-5(4H)-ones into Enantiomerically Enriched α-Amino Acid Derivatives," The Journal of Organic Chemistry, Feb. 2014, vol. 79, No. 4, pp. 1542-1554.
Michels "Targeting the Trimolecular Complex for Immune Intervention," ATDC 2014 Keystone Conference, Jul. 18, 2014, [retrieved online from: www.ucdenver.edu/academics/colleges/medicalschool/centers/BarbaraDavis/Documents/ATDC%202014%20Slides/3.4%20Michels%20Targeting%20Trimolecular%20Complex.pdf].
Mordes et al., "Rat Models of Type 1 Diabetes: Genetics, Environment, and Autoimmunity," ILAR Journal, 2004, vol. 45, No. 3, pp. 278-291.
Moriyama et al., "Evidence for a primary islet autoantigen (preproinsulin 1) for insulitis and diabetes in the nonobese diabetic mouse," Proc. Natl Acad. Sci. USA, 2003, vol. 100, pp. 10376-10381.
Moseman et al., "Human Plasmacytoid Dendritic Cells Activated by CpG Oligodeoxynucleotides Induce the Generation of CD4+CD25+ Regulatory T Cells," The Journal of Immunology. 2004, vol. 173, pp. 4433-4442.
Nakayama et al., "Prime role for an insulin epitope in the development of type 1 diabetes in NOD mice," Nature, 2005, vol. 435(7039), pp. 220-223, author manuscript, 10 pages.
Nakayama et al., "Priming and effector dependence on insulin B:9-23 peptide in NOD islet autoimmunity," J. Clin. Invest., 2007, vol. 117, pp. 1835-1843.
Nakayama et al., "Regulatory vs. inflammatory cytokine T-cell responses to mutated insulin peptides in healthy and type 1 diabetic subjects," PNAS, 2015, vol. 112(14), pp. 4429-4434.
Oikonmakos et al., "Allosteric inhibition of glycogen phosphorylase alpha by the potential antidiabetic drug 3-isopropyl 4-(2-chorophenyl)-1,4-dihydro-1-ethyl-2-methyl-pyridine-3,5,6-tricarboxylate," Protein Science, 1999, vol. 8, pp. 1930-1945.
Orban et al., "Autoantigen-specific regulatory T Cells induced in patients with Type 1 Diabetes Mellitus by Insulin B-chain immunotherapy," Journal of Autoimmunity, 2010, vol. 34(4), pp. 408-415, 21 pages.
Pietropaolo et al., "Primer: Immunity and Autoimmunity," Diabetes, 2008, vol. 57, pp. 2872-2882.
Puri et al., "Modulation of the Immune Response in Multiple Sclerosis," J. Immunol., 1997, vol. 158, pp. 2471-2476.
Renwick et al., "The Absorption and Conjugation of Methyldopa in Patients with Celiac and Crohn's Diseases During Treatment," Br. J. Clin. Pharmac., 1983, vol. 16, pp. 77-83.
Rosenblum et al., "Treating Human Autoimmunity: Current Practice and Future Prospects," Sci Transl Med, 2012, 4(125), 125sr1, pp. 1-20.
Sakaguchi et al., "Immunologic self-tolerance maintained by activated T cells expressing IL-2 receptor alpha-chains (CD25), Break-down of a single mechanism of self-tolerance causes various autoimmune diseases," The Journal of Immunology, 1995, vol. 155(3), pp. 1151-1164c.
Salvati et al., "Recombinant human interleukin 10 suppresses gliadin dependent T cell activation in ex vivo cultured coeliac intestinal mucosa," Gut, 2005, retrieved from gut.bmj.com, retrieved on Aug. 21, 2012, vol. 54, pp. 46-53.
Savoie et al., "Use of BONSAI decision trees for the identification of potential MHC class I peptide epitope motifs," Pacific Symposium on Biocomputing, 1999, vol. 4, pp. 182-189, 8 pages.
Scheen, "Pathophysiology of type 2 diabetes," Acta Clinica Belgica, 2003, vol. 58(6), pp. 335-341.
Sharma et al. "Gastroretentive Drug Delivery System: An Approach to Enhance Gastric Retention for Prolonged Drug Release," International Journal of Pharmaceutical Sciences and Research, 2014, vol. 5(4), pp. 1095-1106.
Sjoerdsma et al., "Studies on the Metabolism and Mechanism of Action of Methyldopa," Circulation, 1963, vol. 28, pp. 492-502.
Sosinowski et al., "Type 1 diabetes: primary antigen/peptide/register/trimolecular complex," Immunologic Research, 2013, vol. 55, pp. 270-276.
Stadinski et al., "Diabetogenic T cells recognize insulin bound to IAg7 in an unexpected, weakly binding register," PNAS, 2010, vol. 107(24), pp. 10978-10983.
Stern et al., "Action of α-methyldopa on the intention tremor," Arzneimittel-Forschung, 1970, vol. 20(5), pp. 727-728.
Suri et al, "Natural peptides selected by diabetogenic DQ8 and murine I-A g7 molecules show common sequence specificity," The Journal of Clinical Investigation, 2005, vol. 115(8), pp. 2268-2276.
Suri et al., "The Murine Diabetogenic Class II Histocompatibility Molecule I-A (g7): Structural and Functional Properties and Specificity of Peptide Selection," Adv. Immunol., 2005, vol. 88, pp. 235-265.
Suri-Payer et al., "CD4+CD25+ T Cells Inhibit Both the Induction and Effector Function of Autoreactive T Cells and Represent a Unique Lineage of Immunoregulatory Cells" The Journal of Immunology, 1998, vol. 160, pp. 1212-1218.
Thomson et al., "FK 506: a novel immunosuppressant for treatment of autoimmune disease: Rationale and preliminary clinical experience," Springer Semin Immunopathol. 1993, vol. 14(4), 31 pages.
Todd et al., "A molecular basis for MHC class II associated autoimmunity," Science, 1988, vol. 240, pp. 1003-1009.
Vandenbark et al., "Treatment of multiple sclerosis with T-cell receptor peptides: Results of a double-blind pilot trial," Nature Medicine, 1996, vol. 2, pp. 1109-1115.
Wallis et al., "Type 1 Diabetes in the BB rat: A polygenic disease," Diabetes, 2009, vol. 58(4), pp. 1007-1017.
Wang et al., "Immunopharmacological and antitumor effects of second-generation immunomodulatory oligonucleotides containing synthetic CpR motifs," International Journal of Oncology, 2004, vol. 24, pp. 901-908.
Wicker et al., "Type 1 diabetes genes and pathways shared by humans and NOD mice," J. Autoimmun., 2005, vol. 25 (Suppl), pp. 29-33.
Wucherpfennig, "Insights into autoimmunity gained from structural analysis of MHC-peptide complexes," Current Opinion in Immunology, 2001, vol. 13, pp. 650-656.
Zhang et al., "Immunization with an insulin peptide-MHC complex to prevent type 1 diabetes of NOD mice," Diabetes Meta Res Rev, 2011, vol. 27, pp. 784-789.
Zhong et al., "Production, specificity, and functionality of monoclonal antibodies to specific peptide-major histocompatibility complex class II complexes formed by processing of exogenous protein," Proc. Natl. Acad. Sci. USA, 1997, vol. 94, pp. 13856-13861.
International Search Report and Written Opinion for International (PCT) Application No. PCT/US2016/013252, dated Mar. 30, 2016, 11 pages.
International Patentability Search Report for International (PCT) Application No. PCT/US2016/013252, dated Jul. 27, 2017, 10 pages.
Extended European Search Report for European Patent Application No. 16737819.9, dated Mar. 1, 2019, 7 pages.

(56) References Cited

OTHER PUBLICATIONS

International Search Report and Written Opinion for International (PCT) Application No. PCT/US2017/23571, dated Jul. 3, 2017, 17 pages.
International Search Report and Written Opinion for International (PCT) Application No. PCT/US2012/039849, dated Sep. 21, 2012, 9 pages.
International Preliminary Report on Patentability for International (PCT) Application No. PCT/US2012/039849, dated Dec. 5, 2013, 7 pages.
International Search Report and Written Opinion for International (PCT) Application No. PCT/US2016/034527, dated Aug. 25, 2016, 13 pages.
International Preliminary Report on Patentability for International (PCT) Patent Application No. PCT/US2016/034527, dated Dec. 7, 2017 12 pages.
Official Action for Canada Patent Application No. 2,980,940, dated Jul. 9, 2018 4 pages.
Official Action for U.S. Patent Application No. 2,980,940, dated Apr. 1, 2019 9 pages.
Extended European Search Report for European Patent Application No. 16800769.8, dated Jan. 8, 2019, 16 pages.
Official Action for U.S. Appl. No. 15/541,074, dated Apr. 16, 2018 5 pages, Restriction Requirement.
Official Action for U.S. Appl. No. 15/541,074, dated Aug. 28, 2018 10 pages.
Notice of Allowance for U.S. Appl. No. 15/541,074, dated Mar. 28, 2019, 5 pages.
Corrected Notice of Allowance for U.S. Appl. No. 15/541,074, dated Apr. 26, 2019 2 pages.
Official Action for U.S. Appl. No. 15/466,026, dated May 17, 2017 24 pages.
Notice of Allowance for U.S. Appl. No. 15/466,026, dated Oct. 13, 2017 8 pages.
Official Action for U.S. Appl. No. 15/894,118, dated May 14, 2018 8 pages, Retriction Requirement.
Official Action for U.S. Appl. No. 15/894,118, dated Aug. 2, 2018 18 pages.
Notice of Allowance for U.S. Appl. No. 15/894,118, dated Dec. 6, 2018 10 pages.
Official Action for U.S. Appl. No. 16/357,397, dated Jul. 12, 2019 8 pages Restriction Requirement.
Official Action for U.S. Appl. No. 14/119,926, dated May 21, 2015 6 pages, Restriction Requirement.
Official Action for U.S. Appl. No. 14/119,926, dated Nov. 3, 2015 19 pages.
Notice of Allowance for U.S. Appl. No. 14/119,926, dated Jul. 26, 2016 7 pages.
Notice of Allowance for U.S. Appl. No. 14/119,926, dated Aug. 19, 2016 5 pages.
Official Action for U.S. Appl. No. 15/556,710, dated Mar. 29, 2018 11 pages, Restriction Requirement.
Official Action for U.S. Appl. No. 15/556,710, dated Oct. 3, 2018 18 pages.
Official Action for U.S. Appl. No. 15/556,710, dated May 31, 2019 13 pages.
Valenta et al. "α-Benzyldopamine and some related compounds: Synthesis and pharmacological screening" Collection of Czechoslovak Chemical Communications, 1984, vol. 49, No. 4, pp. 1002-1008.
Official Action for European Patent Application No. 17715858.1, dated Dec. 18, 2019 5 pages.
Official Action for European Patent Application No. 17715858.1, dated Jul. 27, 2020 3 pages.
Official Action for Canada Patent Application No. 2,980,940, dated Dec. 11, 2019 3 pages.
Notice of Allowance for Canada Patent Application No. 2,980,940, dated Aug. 7, 2020 1 page.
Official Action for European Patent Application No. 16800769.8, dated Jul. 1, 2020 6 pages.
Official Action for U.S. Appl. No. 16/357,397, dated Oct. 24, 2019 19 pages.
Official Action for U.S. Appl. No. 16/357,397, dated Mar. 16, 2020 15 pages.
Official Action for U.S. Appl. No. 16/357,397, dated Sep. 14, 2020 7 pages.
Official Action for U.S. Appl. No. 15/556,710, dated Oct. 15, 2019 10 pages.
Official Action for U.S. Appl. No. 15/556,710, dated Mar. 4, 2020 11 pages.
U.S. Appl. No. 14/119,926, filed Jul. 28, 2014 now U.S. Pat. No. 9,629,848.
U.S. Appl. No. 14/341,767, filed Jul. 26, 2014.
U.S. Appl. No. 15/355,738, filed Nov. 18, 2016.
U.S. Appl. No. 15/495,132, filed Apr. 24, 2017.
U.S. Appl. No. 15/556,710, filed Sep. 8, 2017.
U.S. Appl. No. 15/466,026, filed Mar. 22, 2017 now U.S. Pat. No. 9,820,957.
U.S. Appl. No. 15/817,739, filed Nov. 20, 2017.
U.S. Appl. No. 15/894,118, filed Feb. 12, 2018 now U.S. Pat. No. 10,258,591.
U.S. Appl. No. 16/357,397, filed Mar. 19, 2019.
U.S. Appl. No. 15/541,074, filed Jun. 30, 2017.

* cited by examiner

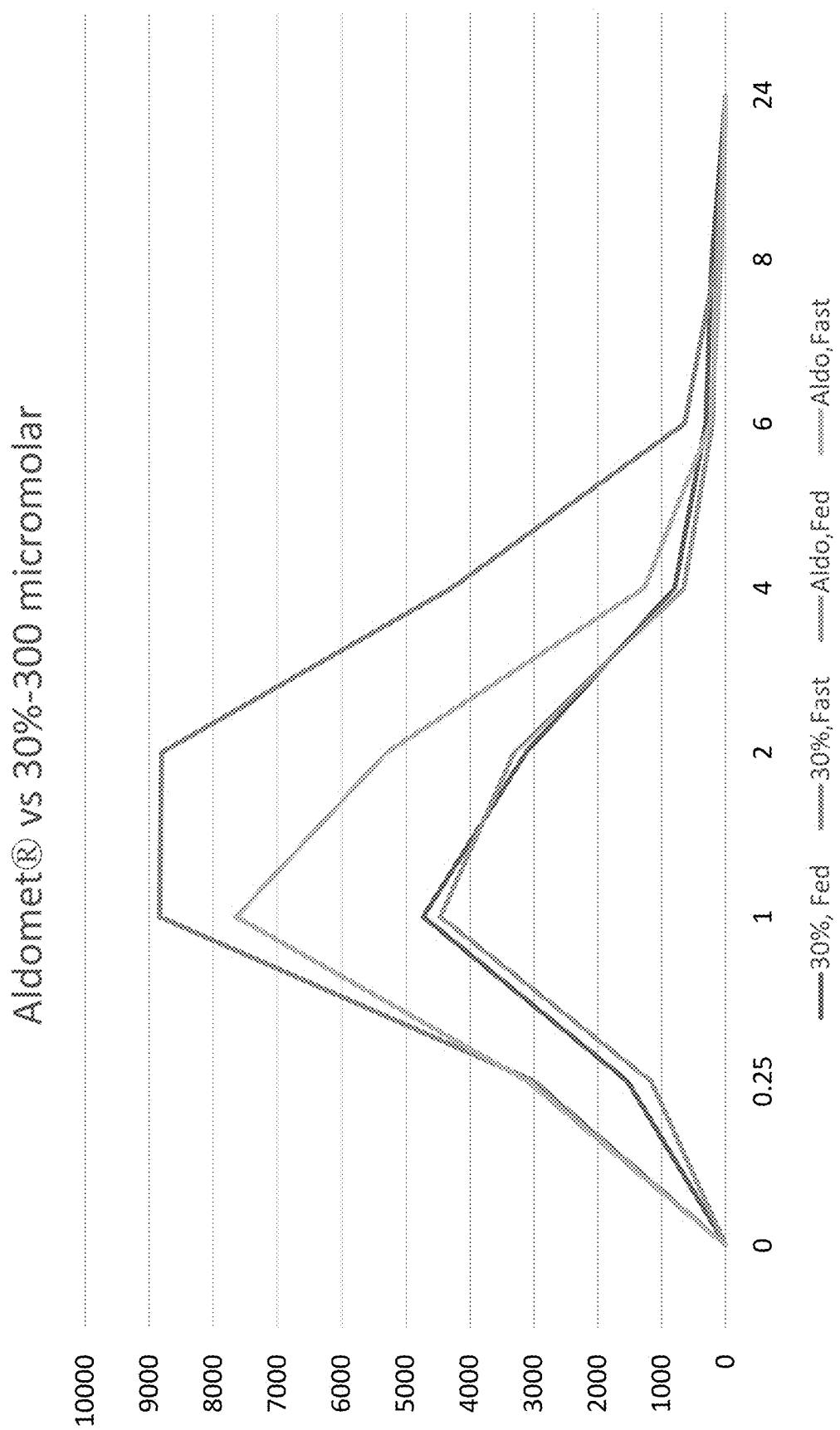

ADMINISTRATION OF ORAL METHYLDOPA

TECHNICAL FIELD

The invention relates to methods of administering alpha-methyldopa, or its salts, that significantly enhance the bioavailability of the drug.

BACKGROUND

There are numerous advantages to enhanced bioavailability of an oral drug delivery method, including the improvement in efficacy following administration, reducing the required frequency of administration, which results in improved patient compliance. The effects of drug therapy depend not only on the drug release pattern from the formulation, but also on the kinetics of drug absorption from the gastrointestinal tract. The absorption of a drug from the gastrointestinal tract is dictated by the location of the dosage form in the gastrointestinal tract, the GI contents, and, in the case of some drugs, the existence and function of active transport mechanisms. Some drugs are more efficiently absorbed from the upper part of the GI tract while others are absorbed from the lower parts of the gastro-intestinal tract. For drugs absorbed only in the stomach or certain regions of the small intestine (called "windows of absorption"), once such drugs pass this region, very little or no drug absorption takes place. Therefore, in instances where the drug is not absorbed uniformly throughout the gastro-intestinal tract, the rate of drug absorption will not be constant in spite of the drug delivery system delivering the drug at constant rates into the gastro-intestinal fluids.

SUMMARY

Alpha-methyldopa is widely used in the treatment of hypertension, but it is known to be incompletely absorbed from the gastrointestinal tract. The fraction of the dose available to the systemic circulation as free α-methyldopa averages only 25% after an oral solution and 27% when administered as tablets (Merfeld A E, et al., *The effect of pH and concentration on alpha-methyldopa absorption in man*, J Pharm Pharmacol. 1986; 38(11):815-22). Oral bioavailability in man also varies greatly, ranging from 8 to 62% of the dose, and studies have found that percentage absorbed varies by a factor of at least 3. Furthermore, in a replicate dosing study, the intra-subject variability was nearly as high as inter-subject variability in bioavailability (Schrogie, et al., Clin. Pharmacol. Ther., 1979; 25:248). Although the incomplete bioavailability of α-methyldopa can be partially attributed to poor absorption and to first-pass metabolism in the gut wall, the underlying causes for its limited bioavailability have also been attributed to both pH- and concentration-dependent absorption of α-methyldopa from the stomach or upper intestine. Thus, enhanced absorption of the drug from an oral methyldopa dosage form could provide improved α-methyldopa bioavailability.

α-Methyldopa is structurally similar to the neutral amino acids which are absorbed from the intestine by a concentration-dependent, saturable, active transport mechanism. These absorption effects, as well as a weak pH dependency were confirmed in an open crossover study in which a triple lumen perfusion tube was used in normal adult male volunteers perfused with buffered solutions of α-methyldopa at three pH values and three concentrations (Merfeld A E, et al., supra). The data from this study indicated that α-methyldopa is absorbed via a non-passive transport process.

Under normal or average conditions, material passes through the small intestine in as little as 1 to 3 hours. Thus, for drugs that are absorbed almost exclusively in the proximal small intestine, such as α-methyldopa, the short contact time in the stomach and intestine greatly limits the bioavailability. Such drugs will have their greatest bioavailability, and therefore their greatest therapeutic effect when absorption from the small intestine is increased. Delivery of methyldopa in this manner may provide greater therapeutic effects without the need for repeated dosages, or with a lower dosage frequency.

In medical care, the timing of drug administration relative to ingestion of food is very important. If a sustained release medication is administered after a meal, the migrating drug dosage complex is interrupted by the food and the dosage form may remain in the stomach for 12 hours or more, which provides an opportunity for drug to be absorbed. However, if the drug dosage form is administered on an empty stomach, it may empty into the intestine in as little as 20 minutes and be transported through the small intestine in less than 3-5 hours. This can result in dramatically decreased drug absorption for drugs with an absorption window or drugs that are not absorbed if they are not well dissolved in gastric fluid before transfer into the small intestine. Thus, the same medication may have very different bioavailability, and therefore produce quite different results, depending on whether the medication is taken on a fed or fasted stomach. For example, polar nutrients, such as amino acids and di- or tri-peptides, are absorbed by special transport carriers in the human small intestine located both in the brush border and basolateral membranes (referred to as the large neutral amino acid transporters). In man, a few drugs, such as levodopa, α-methyldopa, riboflavin, amino-β-lactam antibiotics, and ACE-inhibitors are believed to utilize these transport systems. In animal studies, these drugs have been shown to be actively transported across the intestinal mucosa. Methyldopa competes with other large neutral amino acids in food for the active transporters in the proximal small intestine, while levodopa and carbidopa are not competitors for these active transport pathways.

The inventors have surprisingly found that methyldopa, despite the fact that the drug is primarily absorbed from the small intestine, has enhanced oral bioavailability when administered on an empty stomach (i.e., administered to a subject in a fasted state). This is in direct contrast to the expected dramatic decrease in methyldopa absorption that is expected for drugs like methyldopa that have an absorption window in the upper (proximal) region of the small intestine, as explained above.

Enhancing absorption of α-methyldopa in the most efficient site of absorption allows for more effective and consistent oral absorption of α-methyldopa.

Other aspects of the invention will be set forth in the accompanying description of embodiments, which follows and will be apparent from the description. However, it should be understood that the following description of embodiments is given by way of illustration only, as various changes and modifications within the spirit and scope of the invention will become apparent to those skilled in the art and are encompassed within the scope of this disclosure.

BRIEF DESCRIPTION OF DRAWING

FIG. 1 shows the plasma concentration of α-methyldopa in rats following oral administration of the immediate-release reference dosage form (ALDOMET®, "Aldo") and an extended release dosage formulation containing 30% α-methyldopa ("30%"), in the fed and fasted state.

DESCRIPTION OF EMBODIMENTS

The present disclosure provides oral α-methyldopa administration methods that enhance the bioavailability of the administered α-methyldopa.

Unless otherwise indicated, this disclosure uses the following definitions:

"About," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

"Subject" refers to a mammal, including a human.

"Pharmaceutically acceptable" substances refer to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Treating" generally refers to reversing, alleviating, inhibiting the progress of, or preventing a disorder or condition in a subject, or to preventing one or more symptoms of such disorder or condition in the subject. "Treatment" refers to the act of "treating" as defined immediately above.

"Drug," "drug substance," "active pharmaceutical ingredient," and the like, refer to a compound (e.g., α-methyldopa) that may be used for treating a subject in need of such treatment.

"Therapeutically effective amount" of a drug refers to the quantity of the drug that may be used for treating a subject and is generally in the range of about 0.001 to about 100 mg/kg/day for an adult, and is often in the range of about 0.1 to about 50 mg/kg/day for an adult. For an adult human, a typical daily dose of a drug is in the range of about 0.5 mg to about 2000 mg. For α-methyldopa, the daily dose for an adult human may be in the range of about 0.5 mg to about 4000 mg, and is often in the range of about 50 mg to about 2000 mg.

"Inert" substances refer to those substances that may influence the bioavailability of the drug, but are otherwise pharmaceutically inactive.

"Excipient" or "adjuvant" refers to any inert substance used within the pharmaceutical compositions of this disclosure.

"Pharmaceutical composition" refers to the combination of one or more drug substances and one or more excipients.

"Drug product," "pharmaceutical dosage form," "dosage form," "final dosage form" and the like, refer to a pharmaceutical composition that is administered to a subject in need of treatment and generally may be in the form of tablets, capsules, sachets containing powder, or granules, liquid solutions or suspensions, patches, and the like.

"Solvate" describes a molecular complex comprising the drug substance (e.g., α-methyldopa) and a stoichiometric or non-stoichiometric amount of one or more pharmaceutically acceptable solvent molecules (e.g., ethanol). When the solvent is tightly bound to the drug the resulting complex will have a well-defined stoichiometry that is independent of humidity. However, when the solvent is weakly bound, as in channel solvates and hygroscopic compounds, the solvent content will be dependent on humidity and drying conditions. In such cases, the complex will often be non-stoichiometric.

"Hydrate" describes a solvate comprising the drug substance and a stoichiometric or non-stoichiometric amount of water. The sesquihydrate is a preferred hydrate form of α-methyldopa.

"Release," "released," and the like, when used in reference to a pharmaceutical composition or dosage form, refers to the portion of the drug substance that leaves the dosage form following contact with an aqueous environment. Unless otherwise indicated, the quantity of drug released from a dosage form is measured by dissolution testing in water (37° C., initial pH of 6.8, using standard apparatus) as described the United States Pharmacopeia, 28th Revision, Chapter 711, Second Supplement, (Aug. 1, 2005 to Dec. 31, 2005). The results of the dissolution testing are reported as % (w/w) released as a function of time or as the release time, tN, where N is the % (w/w) of drug released or dissolved. For the purposes of this disclosure, complete drug release occurs when at least 90% of the drug has been released from the dosage form (i.e., at t90).

As used herein, a "fasted" patient, "fasting conditions" or "fasting" refers to a patient who has not eaten any food, i.e., who has fasted for at least 2 hours, or preferably, 3 hours, 4 hours, 5 hours, 6 hours, 7 hours, 8 hours, 9 hours, or 10 hours, before the administration of an oral formulation of the present disclosure comprising at least one active agent (e.g., α-methyldopa) and who does not eat any food, and continues to fast for at least 2 hours, or preferably longer, after the administration of the formulation. The formulation may be administered with 240 ml of water during the fasting period, and water can be allowed ad libitum before, during, or after ingestion of an oral formulation of the present disclosure.

As used herein, a "fed subject", "fed conditions" or "fed" refers to a subject who consumes a meal 2 hours, or less, before ingesting an oral formulation of the present disclosure, or a subject who consumes a meal within 2 hours of ingesting an oral formulation of the present disclosure. Similarly, under fed conditions, water can be allowed ad libitum before, during, and after ingestion.

"Steady-state," when used in reference to the pharmacokinetic (PK) parameters such as the minimum (Cmin) and maximum (Cmax) concentrations of the drug substance in the blood plasma of the subject, refers to the nearly constant values of the PK parameters that result from repeated administration of a dosage form at uniform dosing intervals. For dosage forms containing α-methyldopa, steady-state values of Cmax and Cmin usually occur about 24 to 48 hours following first administration.

LIST OF ABBREVIATIONS

Abbreviation Description
API active pharmaceutical ingredient, (i.e., α-methyldopa)
Cmax maximum concentration of API in subject's plasma
Cmin minimum concentration of API in subject's plasma
ER extended release
GI gastrointestinal
n number of samples
PK pharmacokinetic
QD once daily
RPM revolutions per minute
RT room temperature, about 20° C. to 25° C.
s seconds
tR dosage form retention time in subject's stomach tN dosage form drug release (aqueous dissolution) time, where N is % released; N≥90 corresponds to complete release tmax time to reach CMAX following administration USP United States Pharmacopoeia v/v volume/total volume×100, % w/v weight (g)/total volume (mL)×100, % w/w weight (mass)/total weight (mass)×100, %

Any reference in this disclosure to a temperature range, a pH range, a weight (mass) range, a molecular weight range, a percent range, etc., whether expressly using the words "range" or "ranges," includes the indicated endpoints and all points between the endpoints.

As noted above, oral pharmaceutical compositions useful in the methods of this disclosure may comprise an active pharmaceutical ingredient ("API"; α-methyldopa) and excipients. The API may include α-methyldopa or a pharmaceutically acceptable complex, salt, solvate or hydrate thereof. The API generally comprises from about 5% to about 60% of the pharmaceutical composition by weight, which would typically correspond to a solid dosage form (e.g., tablet) that contains from about 5 mg to about 1000 mg of α-methyldopa. Besides α-methyldopa, other useful active pharmaceutical ingredients may include those having a similar half-life (e.g., about 105 minutes) and absorption characteristics in the GI tract (e.g., α-methyldopa is primarily absorbed in the upper intestine via an active transport system).

Pharmaceutical formulations useful in the methods of this disclosure may employ any pharmaceutically acceptable form of α-methyldopa, including its free form (zwitterion), and its pharmaceutically acceptable complexes, salts, solvates, hydrates (esp. the sesquihydrate), and polymorphs. Salts include, without limitation, acid addition salts and base addition salts, including hemisalts. Pharmaceutically acceptable acid addition salts may include nontoxic salts derived from inorganic acids such as hydrochloric, nitric, phosphoric, sulfuric, hydrobromic, hydroiodic, hydrofluoric, phosphorous, and the like, as well as nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc.

Pharmaceutically acceptable base salts may include nontoxic salts derived from bases, including metal cations, such as an alkali or alkaline earth metal cation, as well as amines. For a discussion of useful acid and base addition salts, see S. M. Berge et al., J. of Pharm. Sci., 66:1-19 (1977); see also Stahl and Wermuth, Handbook of Pharmaceutical Salts: Properties, Selection, and Use (2002).

Pharmaceutically acceptable salts of α-methyldopa may be prepared by reacting its free (or zwitterionic) form with a desired acid or base; by removing an acid- or base-labile protecting group from a suitable precursor of α-methyldopa; by ring-opening a suitable cyclic (lactam) precursor using a desired acid or base; or by converting one salt of α-methyldopa to another by reaction with an appropriate acid or base or by contact with a suitable ion exchange column. These transformations are typically carried out in a solvent. The resulting salt may precipitate out and be collected by filtration or may be recovered by evaporation of the solvent. The degree of ionization in the resulting salt may vary from completely ionized to almost non-ionized.

Alpha-methyldopa may exist in unsolvated and solvated forms (including hydrates) and in the form of other multi-component complexes in which the drug and at least one additional component is present in stoichiometric or non-stoichiometric amounts. Multi-component complexes (other than salts and solvates) include clathrates (drug-host inclusion complexes) and pharmaceutical co-crystals. The latter are defined as crystalline complexes of neutral molecular constituents that are bound together through non-covalent interactions. Co-crystals may be prepared by melt crystallization, by recrystallization from solvents, or by physically grinding the components together. See, e.g., Almarsson & Zaworotko, Chem. Comm. 1889-1896 (2004). For a general review of multi-component complexes, see J. K. Haleblian, J. Pharm. Sci. 64(8):1269-88 (1975).

Most amino acids are chiral (designated as 'L' or 'D' wherein the 'L' enantiomer is the naturally occurring configuration) and can exist as separate enantiomers. The USP standard α-methyldopa for antihypertensive therapy is the 'L' enantiomer of α-methyldopa: L-α-Methyl-3,4-dihydroxyphenylalanine (hereinafter "L-α-methyldopa" available commercially under the tradenames ALDOMET™, ALDORIL™, DOPAMET™, DOPEGYT™), and has the chemical structure:

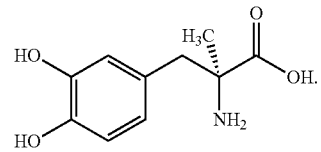

L-α-methyldopa is an alpha-adrenergic agonist (selective for α2-adrenergic receptors) that was developed as a psychoactive drug and has been used extensively as a sympatholytic or antihypertensive.

The 'D' enantiomer of α-methyldopa (D-α-Methyl-3,4-dihydroxyphenylalanine; hereinafter "D-α-methyldopa" is also referred to in the literature as "3-Hydroxy-α-methyl-D-tyrosine"; "D-3-(3,4-Dihydroxyphenyl)-2-methylalanine"; "(+)-α-Methyldopa"; "D-(3,4-Dihydroxyphenyl)-2-methylalanine"; "D-Methyldopa"), has the chemical structure:

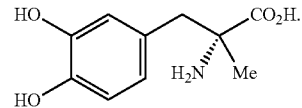

D-α-methyldopa has long been considered to have no pharmacologic activity (see, for example, U.S. Patent Publication No. 2011/0245334, filed Dec. 10, 2009, to Du et al.). Gillespie, et al. (1962, *Clinical and Chemical Studies with α-Methyl-Dopa in Patients with Hypertension*, Circulation 25:281-291) were the first to describe the lack of pharmacological activity in the 'D' isomer and suggest using only the 'L' form for hypertension. Similarly, Sjoerdsma, et al., (1963, *Studies on the Metabolism and Mechanism of Action of Methyldopa*, Circulation, 28:492-502) showed that patients treated with the D enantiomer did not decarboxylate the D enantiomer to α-methyl-dopamine, whereas α-methyl-dopamine did appear in the urine of the same patients treated with the L enantiomer, indicating metabolism of this L enantiomer. Au et al. (1972, *The Metabolism of $^{14}$C-Labelled α-Methyldopa in Normal and Hypertensive Human Subjects*, Biochem. J., 129:1-10) more extensively described the marked differences in metabolism of the two enantiomers in humans, and found that the D isomer was "much less readily absorbed than the active L isomer." These authors cite other supporting literature references, including a suggestion that the optically specific, active transport mechanism that may be responsible for this difference in adsorption. Additionally, Renwick et al. (1983, *The Absorption and Conjugation of Methyldopa in Patients with Coeliac and Crohn's Diseases During Treatment*, Br. J. Clin. Pharmac., 16:77-83) showed that absorption rates of α-methyldopa are different between normal individuals and those with certain GI diseases such as Celiac and Crohn's disease.

Alpha-methyldopa may be prepared using known methods or purchased commercially. Specifically, D-α-methyldopa may be purchased commercially, for example from Toronto Research Chemicals, catalogue M303790. D-α-methyldopa may also be prepared in ways well known to one skilled in the art of organic synthesis, including, for example, by resolution of the racemic form by recrystallization techniques, by synthesis from optically-active starting materials, by chiral synthesis, or by chromatographic separation using a chiral stationary phase. The resolution of α-methyldopa, may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981. Additionally, several methods of effectively and efficiently testing the enantiomeric purity of α-methyldopa are known, as described in Martens, J., et al., *Resolution of Optical Isomers by Thin-Layer Chromatography: Enantiomeric Purity of Methyldopa*, Arch. Pharm. (Weinheim) 319:572-74 (1986); and Gelber, L. R., Neumeyer, J. L., *Determination of the Enantiomeric Purity of Levodopa, Methyldopa, Carbidopa and Tryptophan by the Use of Chiral Mobile Phase High-Performance Liquid Chromatography*, J. Chromatography, 257:317-26 (1983).

Thus, for the purposes of this disclosure, useful forms of α-methyldopa include all of its polymorphs, solvates, hydrates, and crystal habits, the corresponding D- and L-enantiomers of α-methyldopa, and mixtures of the D- and L-enantiomers of α-methyldopa, including a racemic mixture of the corresponding D- and L-enantiomers of α-methyldopa.

In addition, pharmaceutical compositions useful in the methods of this disclosure may employ prodrugs of α-methyldopa. Such prodrugs may be prepared by replacing appropriate functional groups of methyldopa with functionalities known as "pro-moieties," as described, for example, in Bundgaar, H., Design of Prodrugs (1985). Examples of prodrugs would thus include derivatives of α-methyldopa in which an ester group replaces the carboxylic acid group or an amide group replaces the amino group.

Useful forms of α-methyldopa may also include pharmaceutically acceptable isotopically labeled compounds in which one or more atoms are replaced by atoms having the same atomic number, but an atomic mass or mass number different from the atomic mass or mass number that predominates in nature. Examples of isotopes suitable for inclusion in α-methyldopa include isotopes of hydrogen (2H and 3H), carbon (11C, 13C and 14C), and nitrogen (13N and 15N). Isotopically labeled forms of α-methyldopa may generally be prepared by techniques known to those skilled in the art.

In addition to the API, pharmaceutical compositions useful in the methods of this disclosure may include various excipients, including polymers and/or lipids that produce gastro-retentive properties. For oral solid dosage forms (e.g., tablets), these excipients may comprise about 5% to about 90% of the pharmaceutical composition by weight and often comprise about 20% to about 70% of the pharmaceutical composition by weight. In exemplary embodiments, these excipients comprise between 20% and 40% of the pharmaceutical composition, by weight.

Methyldopa extended-release formulations useful in the methods of this disclosure may slowly release the API when ingested and exposed to gastric fluids, and then to intestinal fluids. The controlled-release profile of these formulations can be altered, for example, by varying the amount of controlled-release material, by the inclusion of additional ingredients or excipients, by altering the method of manufacture, etc.

Pharmaceutical compositions useful in the methods of this disclosure are primarily intended to be ingested whole and thereafter begin to release the API when it contacts the gastric fluids in the subject's stomach.

Once daily dosing may be achieved by administering a dosage form that is retained in the stomach for several hours (e.g., $tR \geq 3$, 4, 5, or 6 hours) and releases α-methyldopa over an extended period of time (e.g., $t90>10$, 11, 12, 13, 14, 15, 16, 17, 18, 19, or 20 hours). Such dosage form is typically retained in the subject's stomach for a period of time that ranges from about 3 hours to about 11 hours ($3 \leq tR \leq 11$), from about 6 hours to about 14 hours ($6 \leq tR \leq 14$), or from about 8 hours to about 14 hours ($8 \leq tR \leq 14$), and it releases α-methyldopa over a period of time that ranges from about 3 hours to about 16 hours ($12 \leq t90 \leq 16$), from about 6 hours to about 18 hours ($12 \leq t90 \leq 18$), from about 8 hours to about 20 hours ($12 \leq t90 \leq 20$), from about 14 hours to about 20 hours ($14 \leq t90 \leq 20$), or from about 16 hours to about 20 hours ($16 \leq t90 \leq 20$). Extended release dosage forms may release α-methyldopa over a period of time that is about 4 hours to about 6 hours longer than the time the dosage form is retained in the stomach.

Because eating reduces absorption of α-methyldopa and sleeping decreases GI motility, oral dosage formulations of methyldopa may be administered once daily on an empty stomach (i.e., in a fasted state) or before bedtime (e.g., within about one hour of sleep). To take advantage of both effects and to further enhance drug absorption, the oral dosage forms may be taken on an empty stomach before bedtime (e.g., several hours after an evening meal). For dosage forms taken on an empty stomach, or taken before bedtime, or taken on an empty stomach and before bedtime, the dosage form may be retained in the stomach for times greater than 4 hours, or longer.

Oral methyldopa formulations used in the methods of this disclosure may be administered orally in 1, or 2, or several doses per day. These formulations may be administered in a fasting state (not during the meal, after the meal, or immediately after the meal). These formulations may be administered in a fasting state by administering the formulations to a subject at least 2 hours before, or 2 hours after a meal.

When formulations of α-methyldopa are orally administered, under fasting conditions, the absorption of α-methyldopa may exhibit a Cmax that is at least about 60% greater than the Cmax of α-methyldopa after oral administration to the subject under fed conditions. When formulations of α-methyldopa are orally administered, under fasting conditions, the formulations may exhibit a Cmax that is about 60% to about 125% greater than the Cmax of the formulation after oral administration to the subject under fed conditions. When formulations of α-methyldopa are orally administered, under fasting conditions, the formulations may exhibit a Cmax that is about 60%, 70%, 72%, or 98% greater than the Cmax of the formulation after oral administration to the subject under fed conditions.

When formulations of α-methyldopa are orally administered, under fasting conditions, the absorption of the α-methyldopa may exhibit an AUC that is at least about 10% greater than the AUC of the α-methyldopa after oral administration to the subject under fed conditions. When formulations of α-methyldopa are orally administered, under fasting conditions, the formulations may exhibit an AUC that is about 10% to about 150% greater than the AUC of the formulation after oral administration to the subject under fed conditions. When formulations of α-methyldopa are orally administered, under fasting conditions, the formulations may exhibit an AUC that is about 10%, 15%, 30%, 60%, or 145% greater than the AUC of the formulation after oral administration to the subject under fed conditions.

Methyldopa formulations that are useful in the methods of this disclosure may include systems for extended release of α-methyldopa in the stomach or upper part of the gastrointestinal tract in the form of a composition comprising, or consisting of, between about 50 mg and about 1000 mg of α-methyldopa or a salt thereof. Following oral administration of these delivery systems, the difference in the AUC of the α-methyldopa in the plasma of a subject, when the delivery system is administered orally to the subject in the fed versus the fasted state, may be less than about 15%, or less than about 10%, or less than about 5%, or less than about 3%. Similarly, oral administration of these delivery systems to a subject in a fasted state is bioequivalent to administration of the delivery system to the subject in a fed state, wherein "bioequivalency" is established by a 90% Confidence Interval of between 0.80 and 1.25 for both Cmax and AUC; or a 90% Confidence Interval of between 0.80 and 1.25 for AUC, and a 90% Confidence Interval of between 0.70 to 1.43 for Cmax.

Each publication or patent cited in this disclosure is incorporated herein by reference in its entirety. Additional objects, advantages, and novel features of this disclosure will become apparent to those skilled in the art upon examination of the following examples thereof, which are not intended to be limiting.

EXAMPLES

Example 1

A single dose pharmacokinetic (PK) study was conducted in rats. A 30:30:40 API-Stearic Acid-COMPRITOL® formulation was formed and milled to an average particle size of <300 μm and orally administered to rats (6 per group) in a fasted state. Alpha-methyldopa blood serum levels were measured at various time points up to 24 hours after administration. The commercial, immediate release formulation (ALDOMET®) was tested as a control. The Area Under the Curve (AUC; calculated by the trapezoidal method) are shown in the following table

| Formulation | Fasted AUC (ng) |
|---|---|
| ALDOMET® | 19,504 |
| 30%, 300 μm | 33,208 |

The maximum concentration (Cmax) data are shown in the following table:

| Formulation | Fasted Cmax (ng/ml) | Mean time to Cmax (h) |
|---|---|---|
| ALDOMET® | 7790 | 1.16 |
| 30%, 300 μm | 9428 | 1.5 |

Example 2

This Example demonstrates the pharmacokinetics of absorption of extended release L-α-methyldopa formulations in 60 male Sprague Dawley rats, 8-9 weeks of age. Each rat was identified and tracked with an ear tag. Animals were acclimated for a minimum of 7 days prior to study initiation, and only healthy animals were placed on study. Harlan Teklad Rodent Diet was fed once per day. Water was provided ad libitum.

The in-life portion for this study was 5 days in duration. In-life phase began on Day −3 and ended on Day 1, following the 24-hour blood collection. The day of dosing was designated Day 0. Upon arrival at the testing facility, the rats were placed at random into cages, 3 rats/cage. The rats in Groups 2, 4, 6, 8, and 10 were fasted prior to dosing. Feed was returned at approximately 4 hours following dosing. The rats in Groups 1, 3, 5, 7 and 9 were not fasted. Drug dosage formulations were administered by oral gavage, and the time of dosing was recorded for each animal so that PK time-points could be calculated.

An oral dose level equivalent to a 500 mg dose in a 60 kg adult was used for this study. The rat equivalent dose was based upon the Km factor for rats with a body surface area=$0.025^3$. Body weights were collected prior to dosing on Day −1 for dose calculation and again on Day 0 prior to dosing.

Approximately 300 μL of blood were collected from the jugular vein pre-dose and 0.25, 1, 2, 4, 6, 8, and 24 hours post-dose into K2EDTA microtainer blood collection tubes. Pre-dose blood samples were collected prior to the day of dosing to reduce the number of blood collections required on the day of dosing. Blood samples were collected, thoroughly mixed (gently inverted 8-10 times), and placed one ice. Within 30 minutes of blood collection, blood was centrifuged in a refrigerated centrifuge at approximately 3500 rpm for 10 minutes at 4-8° C., and plasma collected into labeled screw-cap freezer vials. Each vial/tube was labeled with study number, animal ID, date, time point, and sample type (plasma). The sample vials were stored frozen (−70° C.).

The study design of the rats' dose, feeding status, and drug administered is summarized in the following table:

| Group | #/sex | Status | Route | Test Article** | Vehicle | Dose (mg/kg) | Dose volume (mL) | Dose Days | Blood Sample Collection Time |
|---|---|---|---|---|---|---|---|---|---|
| 1 | 6M | Fed | | TA1 ALDOMET ® 500 mg | Water | 50 | 1.0 | | |
| 2 | 6M | Fasted | | TA1 ALDOMET ® 500 mg | Water | 50 | 1.0 | | |
| 3 | 6M | Fed | | TA2 20% MDOPA | Water | *250 | 1.0 | | |
| 4 | 6M | Fasted | | TA2 20% MDOPA | Water | *250 | 1.0 | | Pre-dose, 0.25, 1, 4, 6, 8 and 24 hours post-dose |
| 5 | 6M | Fed | PO | TA3 20% MDOPA 300 µm | Water | *250 | 1.0 | 0 | |
| 6 | 6M | Fasted | | TA3 20% MDOPA 300 µm | Water | *250 | 1.0 | | |
| 7 | 6M | Fed | | TA4 30% MDOPA | Water | *166.7 | 1.0 | | |
| 8 | 6M | Fasted | | TA4 30% MDOPA | Water | *166.7 | 1.0 | | |
| 9 | 6M | Fed | | TA5 30% MDOPA 300 µm | Water | *166.7 | 1.0 | | |
| 10 | 6M | Fasted | | TA5 30% MDOPA 300 µm | Water | *166.7 | 1.0 | | |

*dose corrected for percent α-methyldopa
**Test/control articles were:
TA1: ALDOMET ®: reference (positive control): 500 mg α-methyldopa tablets from Aspen Pharma Trading
TA2: 20:15:65 α-methyldopa-Stearic Acid-COMPRITOL ®, average particle size 75 µm
TA3: 20:15:65 α-methyldopa-Stearic Acid-COMPRITOL ®, average particle size 300 µm
TA4: 30:30:40 α-methyldopa-Stearic Acid-COMPRITOL ®, average particle size 75 µm
TA5: 30:30:40 α-methyldopa-Stearic Acid-COMPRITOL ®, average particle size 300 µm Plasma α-methyldopa concentrations were determined by HPLC-MS detection. The determined area under the curve (AUC), and the peak α-methyldopa plasma concentration attained after administration (Cmax), averaged for each group is shown in the following tables:

| | AUC Fed | AUC Fasted (*) |
|---|---|---|
| ALDOMET ® | 12,263 | 19,504 (60%) |
| TA5 (30:30:40 α-methyldopa-Stearic Acid-COMPRITOL ®, 300 µm) | 13,581 | 33,208 (145%) |

(*) percent increase over AUC Fed

| | Cmax Fed (*) | Cmax Fasted (*) [**] |
|---|---|---|
| ALDOMET ® | 4,522 (1.16 h) | 7,790 (1.16 h) [72%] |
| TA5 (30:30:40 α-methyldopa-Stearic Acid-COMPRITOL ®, 300 µm) | 4,760 (1.17 h) | 9,428 (1.5 h) [98%] |

(*) average time to Cmax
[**] percent increase over AUC Fed

These results demonstrate a very significant increase in α-methyldopa bioavailability following administration under fasting conditions for both the reference dosage form (ALDOMET®) and the dosage formulation containing 30:30:40 methyldopa-Stearic Acid-COMPRITOL®, milled to an average particle size of 300 µm, and administered orally. These results are shown graphically in FIG. 1.

Example 3

This Example demonstrates the pharmacokinetics of absorption of gastro-retentive, extended release L-α-methyldopa formulations in non-naïve male beagle dogs following a single oral capsule administration. Beagle dogs were selected for this study based on their traditional use in pharmacokinetic studies as a non-rodent animal model. Sixteen male non-naïve Beagle dogs ranging in age from 1-5 years were randomly assigned to the different test groups and weighed on the days prior to dosing (Phase 1, Day −1, and Phase 2, Day 6) for the purpose of dose calculation and preparation. A dose level of 15 mg/kg was used to calculate individual doses on a dry weight basis.

The dogs were fed Teklad 25% Global Diet 2025 once per day. Tap water was provided ad libitum. The live phase portion of the study was 12 days in duration, beginning with clinical observations on Day −3 and ending on Day 8 following the 24-hour blood collection. Days on which drug was administered were designated as Day 0 and Day 7.

The dogs were fasted prior to dosing in Phase 1 and were fed 30 minutes prior to dosing in Phase 2. The Test and Reference article(s) were administered orally by placing the capsule at the back of the mouth, the mouth firmly closed, and the throat massaged until the whole capsule was swallowed. Approximately 3-5 mL of water was used to facilitate swallowing.

Test or control article(s) were administered as a single oral dose on Day 0 and Day 7, and the time of dose administration was recorded so PK time points could be calculated. 15 mg/kg α-methyldopa dose level was chosen for this study as this is equivalent to a 500 mg dose in a 60 kg adult human.

Body weights were taken on Day −1, prior to feeding, and on Day 6 approximately 30 minutes after feeding for the purpose of dose calculation and preparation. Fasted body weight was collected prior to dosing on Day 0 and non-fasted body weights were collected prior to dosing on Day 7.

Blood samples were collected pre-dose, and at 0.25, 1, 2, 4, 6, 8, 10, 12, and 24 hours post-dose for each phase of the study. At each time point, whole blood with a volume of approximately 2.4 mL will be collected into K2EDTA (spray dried, 3 mL) plasma tubes, and the reference number noted in the report. All blood samples were taken by jugular vein. The blood tube was gently inverted 8 to 10 times, placed in a chill bucket, centrifuged in a refrigerated centrifuge at approximately 3500 rpm for 10 minutes at 4 to 8° C. Plasma was collected from each sample and transferred as 1 aliquot into a screw-cap freezer vial. Blood was processed for plasma within 1 hour or less from time of blood collection. Plasma was stored at −70° C. Each vial contained at least 150 µl of plasma and was labeled with study number, animal ID, date, and time point.

The study design of the dogs' dose, feeding status, and drug administered is summarized in the following table:

| Group | No/Sex of Animals | Phase | Day of Dose | Feeding status | Route | Article* | Dose (mg/kg) | PK Time points (hours) |
|---|---|---|---|---|---|---|---|---|
| 1 | 4 males | 1 | 0 | Fasted | Oral | ALDOMET ® | 15 | Pre-dose, 0.25, 1, |
| 2 | 4 males | | | | | TA1 | | 2, 4, 6, 8, 10, 12, |
| 3 | 4 males | | | | | TA2 | | and 24 hours |
| 4 | 4 males | | | | | TA3 | | |
| 1 | 4 males | 2 | 7 | Fed | Oral | ALDOMET ® | 15 | |
| 2 | 4 males | | | | | TA1 | | |
| 3 | 4 males | | | | | TA2 | | |
| 4 | 4 males | | | | | TA3 | | |

*Test/control articles were:
ALDOMET ®: reference (positive control): 500 mg α-methyldopa tablets from Aspen Pharma Trading
TA1:: 40:60 α-methyldopa-COMPRITOL ®
TA2:: 30:5:65 α-methyldopa-Stearic Acid-COMPRITOL ®
TA3:: 30:30:40 α-methyldopa-Stearic Acid-COMPRITOL ®

Plasma α-methyldopa concentrations were determined by HPLC-MS detection. The determined area under the curve (AUC) averaged for each group is shown in the following table:

| | AUC Fed | AUC Fasted (*) |
|---|---|---|
| ALDOMET ® | 20,529 | 26,451 (29%) |
| TA3 (30:30:40) | 26,677 | 30,294 (14%) |
| TA2 (30:5:65) | 23,908 | 30,672 (28%) |
| TA1 (40:60) | 29,618 | 31,047 (5%) |
| | (44% increase vs ALDOMET ®) | |

(*) percent increase over AUC Fed

These results demonstrate a significant increase in bioavailability following administration under fasting conditions for the reference dosage form (ALDOMET®) and the two dosage formulations containing stearic acid (30:5:65 α-methyldopa-Stearic Acid-COMPRITOL®; and 30:30:40 α-methyldopa-Stearic Acid-COMPRITOL®).

The dosage formulation containing α-methyldopa and COMPRITOL® (TA1 40:60) showed a very significant increase in bioavailability over the reference dosage form (ALDOMET®) under fed and fasted conditions. Additionally, this 40:60 α-methyldopa-COMPRITOL® formulation showed the greatest absolute bioavailability under both Fed and Fasted conditions.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

What is claimed is:

1. A method of enhancing the bioavailability of methyldopa in a subject comprising administering to the subject an oral D-α-methyldopa dosage formulation and fasting the subject for at least one hour immediately prior to administering the oral D-α-methyldopa dosage formulation, and for at least another 2 hours immediately after administering the oral D-α-methyldopa dosage formulation, wherein the dosage formulation comprises an active pharmaceutical ingredient consisting of D-α-methyldopa.

2. The method of claim 1 wherein the oral D-α-methyldopa dosage formulation, or a pharmaceutically acceptable salt thereof, is administered once daily.

3. The method of claim 1 wherein the oral D-α-methyldopa dosage formulation, or a pharmaceutically acceptable salt thereof, is administered twice daily.

4. The method of claim 1, wherein the oral D-α-methyldopa dose administered ranges from about 50 mg to about 1000 mg.

5. The method of claim 1, wherein the oral D-α-methyldopa dosage formulation is administered with at least 200 ml of water.

6. The method of claim 1, wherein the oral D-α-methyldopa dosage formulation is administered with between 200 ml and 1000 ml of water.

7. The method of claim 1, wherein the subject is a human.

8. The method of claim 1, wherein the oral D-α-methyldopa dosage formulation administered is an immediate release dosage form.

9. The method of claim 1, wherein the oral D-α-methyldopa dosage formulation administered is an extended release dosage form.

10. The method of claim 1, wherein the D-α-methyldopa is selected from salts, solvates, and polymorphs of D-α-methyldopa, and combinations thereof.

11. The method of claim 1, wherein the oral D-α-methyldopa formulation is formulated as a tablet, a caplet, or tablets filled in capsules.

* * * * *